United States Patent [19]

Carceller et al.

[11] Patent Number: 5,420,131
[45] Date of Patent: May 30, 1995

[54] CYANOMETHYLPYRIDINE DERIVATIVES

[75] Inventors: Elena Carceller, Barcelona; Pere J. Jiménez, Tarragona; Carmen Almansa; Javier Bartrolí, both of Barcelona, all of Spain

[73] Assignee: J. Uriach & Cia, S.A., Barcelona, Spain

[21] Appl. No.: 216,583

[22] Filed: Mar. 23, 1994

[30] Foreign Application Priority Data

Mar. 23, 1993 [ES] Spain ..................... 9300591

[51] Int. Cl.$^6$ ............... A61K 31/47; A61K 31/495; C07D 295/00; C07D 401/14
[52] U.S. Cl. ......................... 514/253; 514/314; 544/363; 546/174; 546/175
[58] Field of Search ............ 544/363; 546/174, 175; 514/253, 314

[56] References Cited

U.S. PATENT DOCUMENTS

| | | | |
|---|---|---|---|
| 4,507,297 | 3/1985 | Musaki et al. | 544/386 |
| 4,675,390 | 6/1987 | Bonjouklian et al. | 536/4.1 |
| 4,766,132 | 8/1988 | Kay | 514/332 |
| 4,876,346 | 10/1989 | Musser et al. | 546/172 |
| 4,940,706 | 7/1990 | Bartroli et al. | 514/231 |
| 4,965,266 | 10/1990 | Uno et al. | 544/363 |
| 4,980,362 | 12/1990 | Carceller et al. | 514/336 |
| 5,102,881 | 4/1992 | Zamboni et al. | 544/363 |
| 5,134,151 | 7/1992 | Bartroli et al. | 514/357 |

FOREIGN PATENT DOCUMENTS

| | | |
|---|---|---|
| 146258 | 6/1985 | European Pat. Off. |
| 147768 | 7/1985 | European Pat. Off. |
| 157609 | 10/1985 | European Pat. Off. |
| 138559 | 4/1986 | European Pat. Off. |
| 178261 | 4/1986 | European Pat. Off. |
| 209239 | 1/1987 | European Pat. Off. |
| 210804 | 2/1987 | European Pat. Off. |
| 238202 | 9/1987 | European Pat. Off. |
| 251827 | 1/1988 | European Pat. Off. |
| 254540 | 1/1988 | European Pat. Off. |
| 284359 | 9/1988 | European Pat. Off. |
| 301751 | 2/1989 | European Pat. Off. |
| 312040 | 4/1989 | European Pat. Off. |
| 312041 | 4/1989 | European Pat. Off. |
| 0391624 | 10/1990 | European Pat. Off. |

(List continued on next page.)

OTHER PUBLICATIONS

Pinckard, R. Neal, McManus, Linda M., Halonen, Marilyn, and Hanahan Donald J.: Acetyl glyceryl ether phosphorylcholine: Platelet-activating factor. Int. Arch Allergy appl. Immun. 66 (Suppl. 1): 127–136 (1981).

(List continued on next page.)

*Primary Examiner*—Cecilia Tsang
*Attorney, Agent, or Firm*—Rothwell, Figg, Ernst & Kurz

[57] ABSTRACT

The present invention relates to new cyanomethylpyridine derivatives of formula I

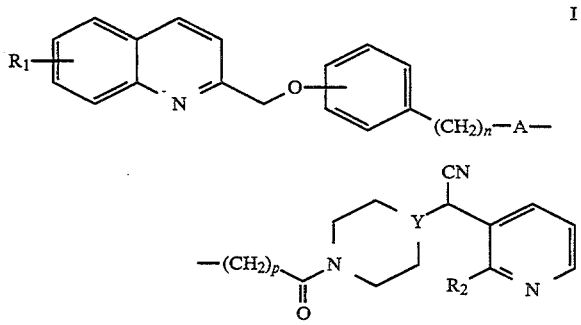

wherein Y represents N or CH; $R_1$ represents hydrogen, fluoro, chloro, difluoro or dichloro; $R_2$ represents hydrogen or $C_{1-4}$ alkyl; n is 0 or 1; p is 0 or 1; A represents a covalent bond or a group of formula —CONHCH(Ar)—, —NHCH(Ar)—, —SO$_2$NHCH(Ar)—, —NHCONHCH(Ar)— or —OCONHCH(Ar)—, and when p is 1, A can also represent —CH(Ar)NH—; and Ar represents phenyl or phenyl substituted with halogen, $C_{1-4}$ alkyl, $C_{1-4}$ alkoxy or trifluoromethyl. These compounds are PAF antagonist and/or 5-lipoxygenase inhibitors.

17 Claims, No Drawings

FOREIGN PATENT DOCUMENTS

| | | |
|---|---|---|
| 441226 | 8/1991 | European Pat. Off. . |
| 528172 | 2/1993 | European Pat. Off. . |
| 0530639 | 3/1993 | European Pat. Off. . |
| 57-165394 | 3/1982 | Japan . |
| 58-35116 | 6/1983 | Japan . |
| 61-93191 | 4/1986 | Japan . |
| 690039 | 7/1969 | South Africa . |
| 2186877 | 8/1987 | United Kingdom . |
| 2200634 | 8/1988 | United Kingdom . |
| 2205833 | 12/1988 | United Kingdom . |
| 8601507 | 3/1986 | WIPO . |
| 92/15294 | 9/1992 | WIPO . |

OTHER PUBLICATIONS

Benveniste, Jacques, Henson, Peter M., and Cochrane, Charles G.: Leukocyte-dependent histamine release from rabbit platelets. The Journal of Experimental Medicine, vol. 136, 1972.

Feuerstein, Glora, Lux, Warren E. Jr., Snyder, Fred, Ezra, David, and Faden, Alan I.: Hypotension produced by platelet-activating factor is reversed by thyrotropin-releasing hormone. Circulatory Shock 13:255-260 (1984).

Roubin, Regine, Tence Martine, Mencia-Huerta, Jean Michel, Arnoux, Bernard, Ninio, Ewa, and Benveniste, Jacques: A chemically defined monokine: Macrophage-derived platelet-activating factor (PAF-Acether). Lymphokines, vol. 8, 1983.

Chacko, George K. and Perkins, Edward G.: Synthesis of Acetal Choline Phosphatide. J. Org. Chem., 32:1623 (1967).

Blank, Merle L., Snyder, Fred, Byers, Lawrence W., Brooks, B., Muirhead, E. Eric: Antihypertensive activity of an alkyl ether analog of phosphatidylcholine. Chemical Abstracts 92:74 (1980).

Hiltrop, K., Stegemeyer, H.: Alignment of liquid crystals by amphiphilic monolayers. Ber. Bunsenges. Phys. Chem. 1978, 82(9), 883-8 (Eng).

Nishihira, Jun, Ishibashi, Teruo, Imai, Yoh, Muramatsu, Toshio: Purification and characterization of the specific binding protein for platelet activating factor (1-O-alkyl-2-=acetyl-sn-glycerol—3-phosphocholine) from human platelets. (Sch. Med, Hokkaido Univ., Sapporo, Japan 060). Tohoku J. Exp. Med. 1985, 146(2), 145-52 (Eng).

Otsuka, A., Masugi, F., Ogihara, T., Saeki, S., Nagano, M., Koyama, Y., Tabuchi, Y., Kumahara, Y.: Prostaglandins, Leukotrienes Med. 1985, 19(1), 25-35 (Eng).

Mazzoni, L., Morley, J., Page, C. P., Sanjar, S.: Induction of airway hyper-reactivity by platelet activating factor in the guinea-pig. Proc. Physiol. Soc. (Mar. 1985), p. 107P.

Merlos, M., Gomez, L. A., Giral, M., Vericat, M. L., Garcia-Rafanell, J. and Forn, J.: Effects of PAF-antagonists in mouse ear oedema induced by several inflammatory agents, *Br. J. Pharmacol.* (1991), 104, 990-994.

Kemeny, L., Csato, M., and Dobozy, A.: Pharmacological studies on dithranol-induced irritative dermatitis in mice. *Arch Dermatol Res.* (1989) 281: 362-365.

Muirhead, E. Eric, Byers, Lawrence W. Desiderio, Dominic, Smith, Keith A., Prewitt, Russell L. and Brooks, Bennie: Alkyl ether analogs of phosphatidylcholine are orally active in hypertensive rabbits. Hypertension 3:3, 1981.

Vargaftig, B. Boris, Chignard, Michel, Benveniste, Jacques, Lefort, Jean, and Wal, Francoise: Background and present status of research on platelet-activating factor (PAF-Acether). Annals New York Academy of Sciences, 1981.

Carceller et al, Chem. Abst. 116:59401y (1992).

Carceller et al, Chem. Abst. 115:256235c (1991).

European Search Report dated Jun. 7, 1994 for corresponding European application No. 94104612.0.

CYANOMETHYLPYRIDINE DERIVATIVES

FIELD OF THE INVENTION

The present invention relates to new cyanomethylpyridine derivatives which are potent PAF (platelet activating factor) antagonists and/or 5-lipoxygenase enzyme inhibitors. The invention also relates to a process for their preparation, to pharmaceutical compositions containing them and to their use in the treatment of the diseases in which PAF and/or 5-lipoxygenase are involved.

DESCRIPTION OF THE PRIOR ART

The platelet activating factor (PAF) or (1-O-alkyl-2-acetyl-sn-glyceryl-3-phosphorylcholine), also called acetyl glyceryl ether phosphorylcholine (AGEPC) or PAF-acether, is a natural phospholipid synthesized by different cells (basophiles, macrophages, neutrophiles, platelets) and tissues (heart, lung and kidney) of the organism.

PAF was described for the first time as a potent platelet aggregating agent. Later on it was demonstrated to have other biological activities in vivo, such as peripheral vasodilatation, increase of the vascular permeability, induction of bronchoconstriction and hyperreactivity of the respiratory tract. PAF also produces immediate hypotension followed by pulmonary and renal hypertension in rats, guinea pigs, rabbits and dogs, and it has been rated as the most potent ulcerogenic agent described until now.

Consequently, PAF is a mediator that is implicated in a large set of pathological processes in mammals, including humans such as asthma, septic shock, transplant rejection, thrombosis, ulceration, inflammation and renal diseases.

On the other hand, other cellular mediators such as the leukotrienes have been implicated as important mediators in several inflammmatory diseases such as asthma, rheumatoid arthritis, psoriasis and inflammatory bowel disease. The leukotrienes are the resulting products of the oxidation of arachidonic acid through the action of the enzyme 5-lipoxygenase. It has been postulated that compounds that act as inhibitors of this enzyme thereby preventing the synthesis of leukotrienes could offer great promise as therapeutic agents in the treatment of those disorders.

In light of this, compounds that exhibit a dual activity as PAF antagonists and 5-lipoxygenase inhibitors could be extremely useful therapeutic agents in the treatment of complex pathologies such as asthma, allergic disorders and other inflammatory diseases.

The closest prior art from the structural point of view is believed to be the compounds disclosed in our patent applications EP 441226 and EP 528172, which relate to cyanomethylpyridines with PAF antagonist activity. Unlike the products disclosed therein, the compounds of the present invention also possess 5-lipoxygenase inhibitor activity. Their ability to affect two different pathways to inflammatory disorders makes them extremely useful as medicinal agents.

DESCRIPTION OF THE INVENTION

The present invention relates to novel cyanomethylpyridine derivatives of general formula I as racemates, diastereoisomer mixtures or in optically active form

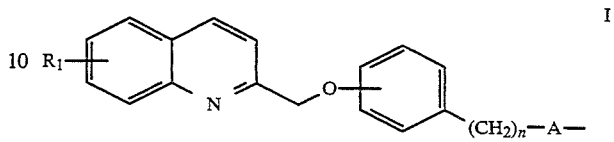

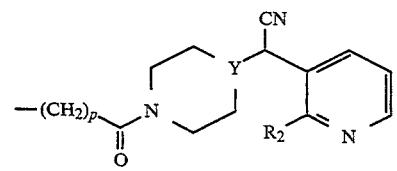

wherein:
Y represents N or CH;
$R^1$ represents hydrogen, fluoro, chloro, difluoro or dichloro;
$R^2$ represents hydrogen or $C_{1-4}$ alkyl;
n is 0 or 1;
p is 0 or 1;
A represents a covalent bond or a group of formula —CONHCH(Ar)—, —NHCH(Ar)—, —SO$_2$NHCH(Ar)—, —NHCONHCH(Ar)— or —OCONHCH(Ar)—, and when p is 1, A can also represent —CH(Ar)NH—;
Ar represents phenyl or phenyl substituted with halogen, $C_{1-4}$ alkyl, $C_{1-4}$ alkoxy or trifluoromethyl;
and the salts and solvates thereof.

The invention also provides a pharmaceutical composition which comprises an effective amount of a compound of formula I or a pharmaceutically acceptable salt or solvate thereof and a pharmaceutically acceptable excipient.

The invention further provides the use of a compound of formula I or a pharmaceutically acceptable salt or solvate thereof in the treatment or prevention of diseases in which PAF and/or 5-lipoxygenase are involved. Accordingly, the invention provides a method for treating or preventing diseases in which PAF and/or 5-lipoxygenase are involved in a mammal, which may be a human being, which comprises administering to a mammal in need thereof an effective amount of a compound of formula I or a pharmaceutically acceptable salt or solvate thereof. Preferred is a method for treating or preventing diseases related with allergy and inflammation such as asthma, dermatitis, urticaria, arthritis and psoriasis; inflammatory bowel disease; and ischemia and shock states such as septic shock, anaphylactic shock, hemorrhagic shock and myocardial ischemia.

The invention still further provides a process for preparing a compound of formula I which comprises reacting an acid of general formula II or a reactive derivative thereof, such as the acid chloride,

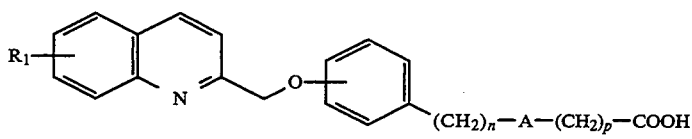

wherein A, $R_1$, n and p have the previously defined meaning, with a compound of formula III

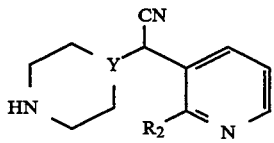

wherein Y and $R^2$ have the previously defined meaning, under standard experimental conditions; or reacting a compound of formula IV

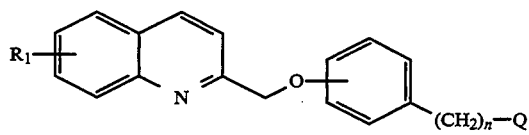

wherein $R_1$ and n have the previously defined meaning and Q means —COOH, —$CO_2Cl$, —OC(=O)$G_1$ (wherein $G_1$ represents a halogen atom or —OPh-), —$SO_2Cl$, —NHC(=O)OPh or —NCO with a compound of formula V

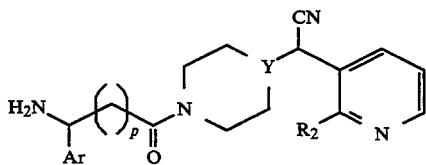

wherein Y, $R_2$, Ar and p have the previously defined meaning, under standard experimental conditions;

and optionally, reacting a compound of formula I with an acid to give the corresponding acid addition salt.

In the above definitions, a $C_{1-4}$ alkyl group means a linear or branched alkyl chain containing from 1 to 4 carbons atoms. It includes methyl, ethyl, propyl, isopropyl, butyl, isobutyl, sec-butyl and tert-butyl, of which methyl and ethyl are preferred and methyl is more preferred.

A $C_{1-4}$ alkoxy group means a group derived from the union of a $C_{1-4}$ alkyl group to an oxygen atom of an ether functional group. Examples includes methoxy, ethoxy, propoxy, isopropoxy, butoxy, isobutoxy, sec-butoxy and tert-butoxy, In the compounds of the present invention, $R_1$ represents hydrogen, fluoro, chloro, difluoro or dichloro. When $R_1$ is different from hydrogen, the substituent(s) are preferably on the 6- and/or 7-positions of the quinoline ring. Thus, the following substitution patterns are preferred: 6-fluoro, 6-chloro, 7-fluoro, 7-chloro, 6,7-difluoro and 6,7-dichloro.

In the compounds of the present invention, $R_2$ is hydrogen or $C_{1-4}$ alkyl, but preferably is hydrogen or methyl.

Preferred embodiments of the present invention are those compounds of formula I wherein the 2-quinolylmethoxy radical is in the para or meta position of the benzene ring and $R_1$, $R_2$, A, Y, n and p have the previously defined meaning.

More preferred embodiments of the present invention are those compounds of formula I wherein the 2-quinolylmethoxy radical is in the para or meta position of the benzene ring, A represents a covalent bond or a group of formula —CONHCH(Ar)— or —CH(Ar)NH—, and $R_1$, $R_2$, Y, n and p have the previously defined meaning.

Still more preferred embodiments of the present invention are those compounds of formula I wherein the 2-quinolylmethoxy radical is in the para or meta position of the benzene ring, A represents a covalent bond or a group of formula —CONHCH(Ar)— or —CH(Ar)NH—, $R^2$ represents hydrogen or methyl, and $R^1$, Y, n and p have the previously defined meaning.

The formulae of some specific compounds are represented below, together with the number corresponding to the example in which their preparation is described:

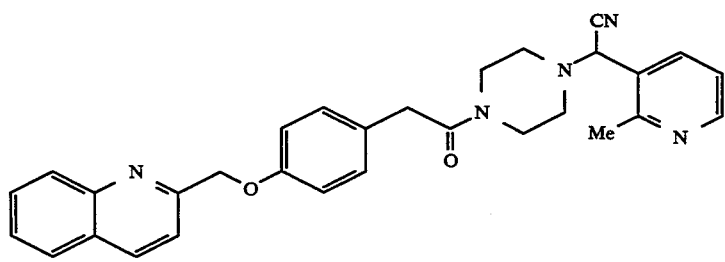

1

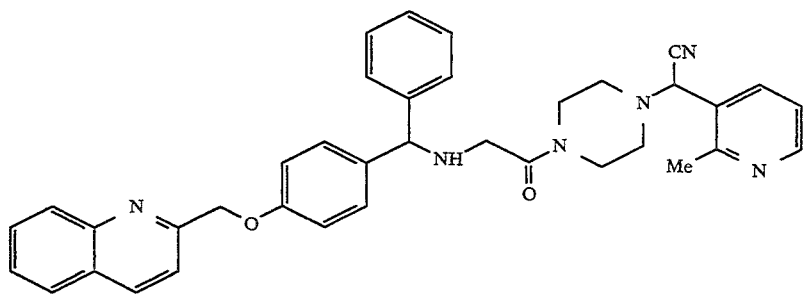
2
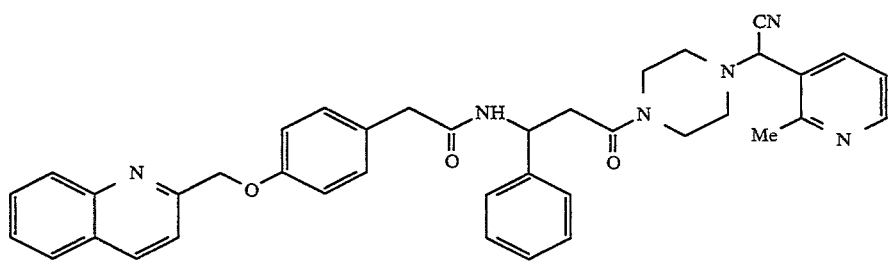
3
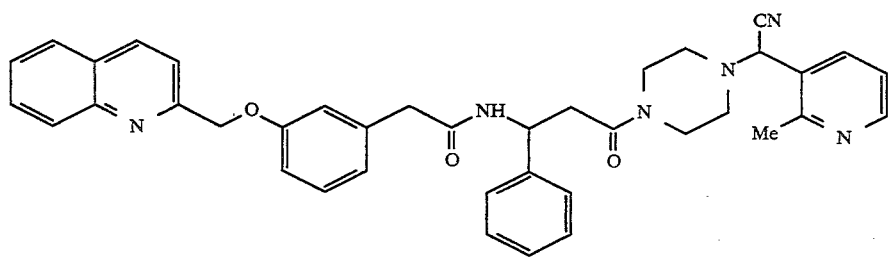
4
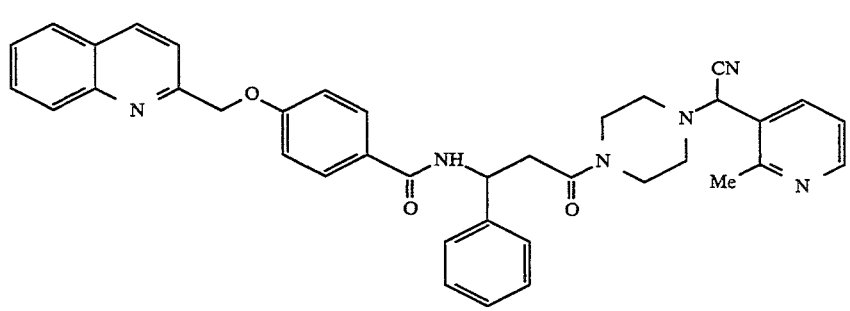
5
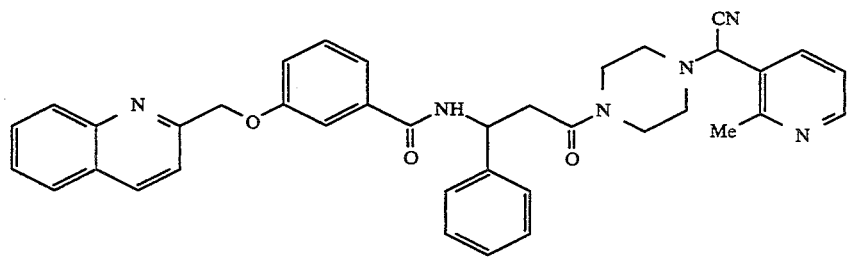
6
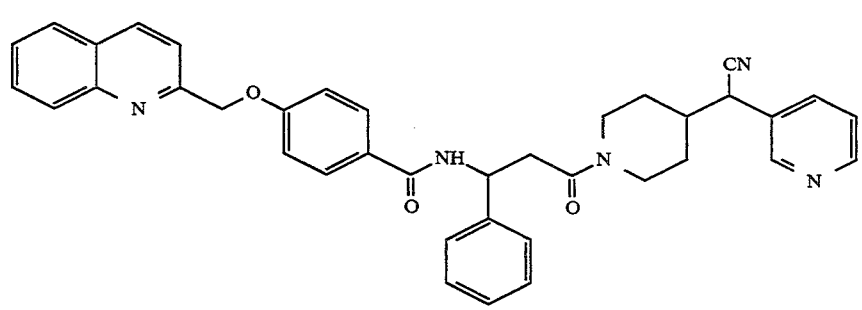
7

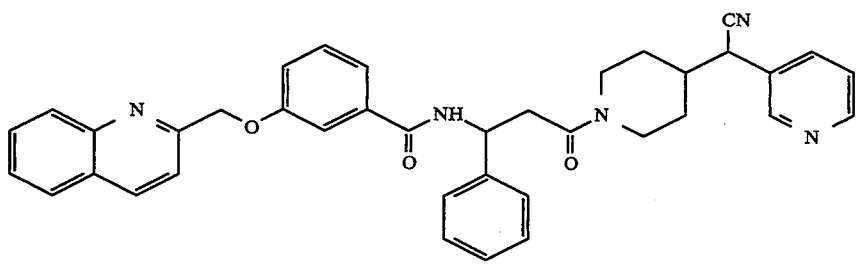

8

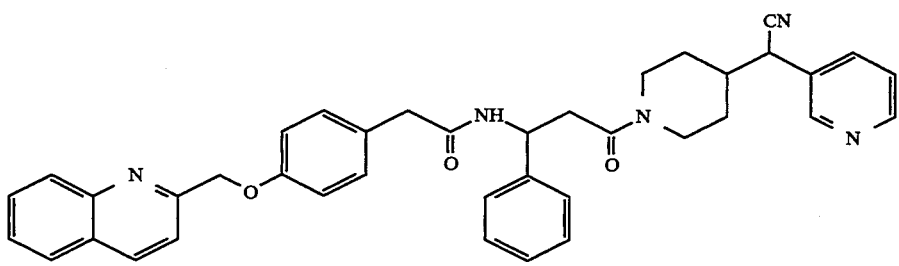

9

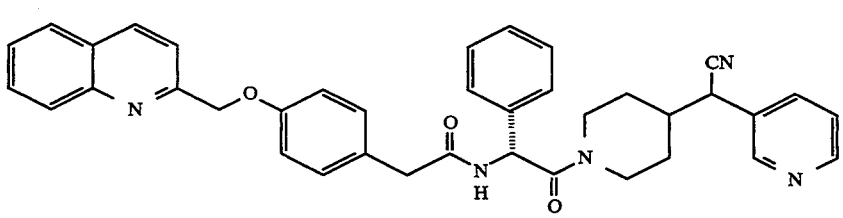

10

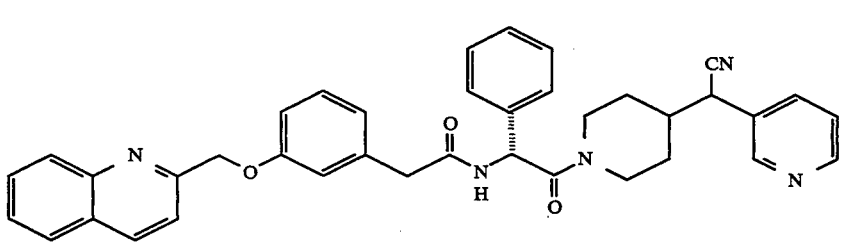

11

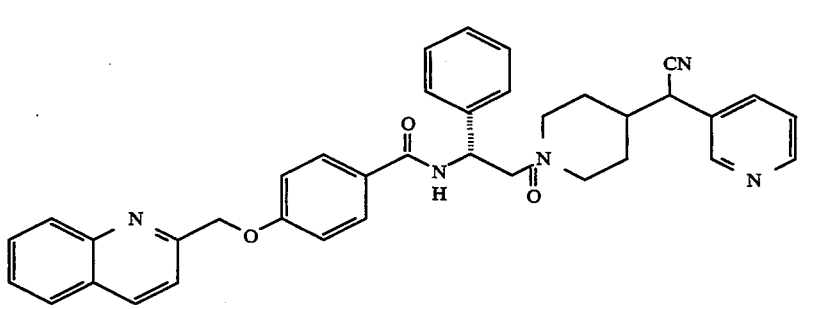

12

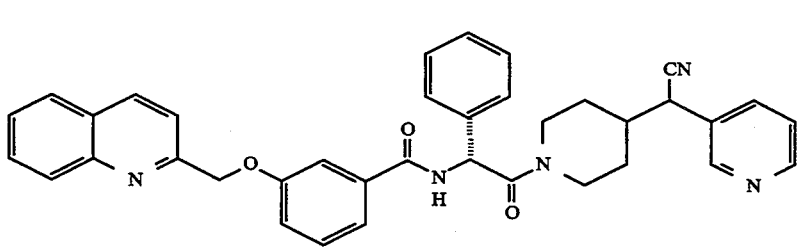

13

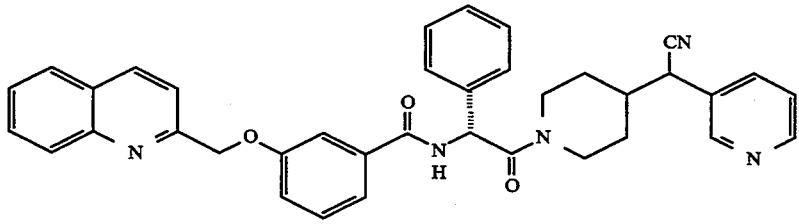

The compounds of formula I contain one or more basic nitrogen atoms and, consequently, they can form salts with acids, which are also included in the present invention. There is no limitation on the nature of these salts, provided that, when used for therapeutic purposes, they are pharmaceutically acceptable, which, as is well-known in the art, means that they do not have reduced activity (or unacceptable reduced activity) or increased toxicity (or unacceptable increased toxicity)

compared with the free compounds. Examples of these salts include: salts with an inorganic acid such as hydrochloric acid, hydrobromic acid, hydriodic acid, nitric acid, perchloric acid, sulfuric acid or phosphoric acid; and salts with an organic acid, such as methanesulfonic acid, trifluoromethanesulfonic acid, ethanesulfonic acid, benzenesulfonic acid, p-toluenesulfonic acid, fumaric acid, oxalic acid or maleic acid. The salts are prepared by reacting the free base with a sufficient amount of the desired acid to produce a salt in the conventional manner. Free bases and their salts differ in certain physical properties, such as solubility, but they are equivalent for the purposes of the invention.

The compounds of the present invention can exist in unsolvated as well as solvated forms, including hydrated forms. In general, the solvated forms, with pharmaceutically acceptable solvents such as water, ethanol and the like, are equivalent to the unsolvated forms for the purposes of the invention.

The compounds of the present invention can exist as different diastereoisomers and/or optical isomers because of the existence of asymmetric carbons in their skeleton. These stereoisomers and the mixtures thereof are all included in the present invention. Diastereoisomers can be separated by conventional techniques such as chromatography or fractional crystallization. The optical isomers can be resolved using any of the conventional techniques of optical resolution to give optically pure isomers. Such a resolution can be performed in any chiral synthetic intermediate as well as in the products of general formula I. The optically pure isomers can also be individually obtained using enantiospecific synthesis. As stated above, the present invention covers the individual isomers as well as their mixtures (e.g. racemic mixtures), whether as obtained by synthesis or by physically mixing them up.

The invention also provides a process for the preparation of the compounds of formula I. The precise method used for the preparation of a given compound of the present invention may vary depending on its chemical structure. The following scheme illustrates the general method for their preparation:

ybenzotriazole and dicyclohexylcarbodiimide to form in situ an activated ester, and subsequently reacting said ester with an amine of formula III. As one skilled in the art recognizes, a wide variety of activated esters can be used in place of that formed by 1-hydroxybenzotriazole. In addition, diimides other than dicyclohexylcarbodiimide can also be employed. The reaction is carried out in a reaction-inert solvent such as dioxane, tetrahydrofuran, acetonitrile, chloroform or N,N-dimethylformamide. The reaction is performed at a temperature ranging from 0° to 60° C. during a period of time from 6 to 24 hours.

b) By reacting amine III with an acid chloride or anhydride derived from an acid of general formula II in the presence of a proton scavenger amine, such as pyridine or triethylamine, in a suitable solvent such as dichloromethane or chloroform, or the same proton scavenger amine can be used as solvent. The reaction is carried out at a temperature between 0° C. and that of the boiling point of the solvent, during a period of time from 30 min to 24 hours. The compounds thus obtained can be purified by standard methods such as flash chromatography or crystallization.

Alternatively, compounds of formula I wherein A represents —CONHCH(Ar)— can also be prepared from a compound of formula IV, wherein $R_1$ and n have the previously defined meaning and Q represents —COOH or —COCl, by reaction with an amine of formula V, wherein Y, $R_2$, Ar and p have the previously defined meaning, under the same experimental conditions mentioned above for the reaction of II with III.

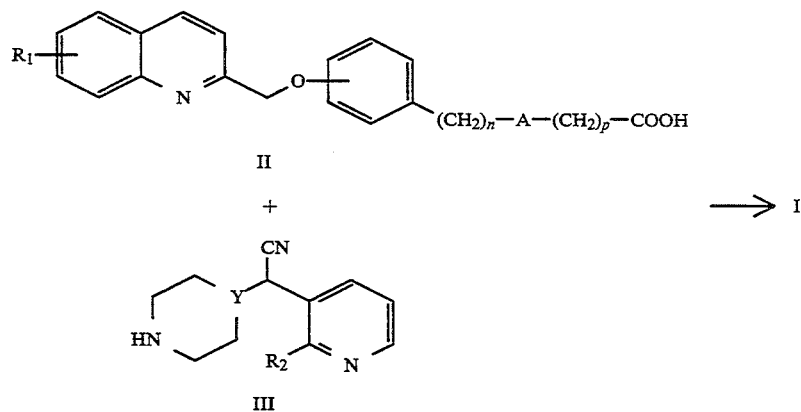

Wherein $R_1$, $R_2$, A, Y, n and p have the previously defined meaning.

Compounds of formula I are prepared by a dehydration procedure between amines of formula III and carboxylic acids of general formula II. This process can be carried out by using any conventional reaction of amide bond formation, such as the following processes: a) By reacting an acid of general formula II with 1-hydrox-

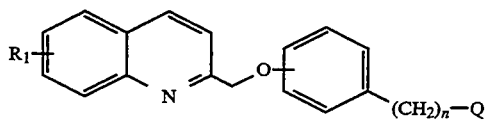

IV

+

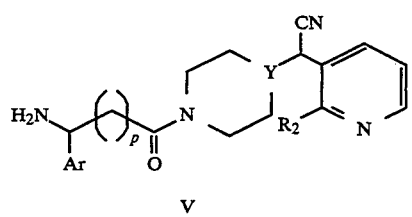

V

Furthermore, compounds of formula I wherein A represents a group of formula —SO$_2$NHCH(Ar-)—, —OCONHCH(Ar)— or —NHCONHCH(Ar)— can also be prepared from a compound of formula IV, wherein R$_1$ and n have the previously defined meaning and Q represents —SO$_2$Cl, —OC(=O)G$_1$ (wherein G$_1$ represents a halogen atom or —OPh), —NHC(=O)OPh or =NCO respectively, by reaction with an amine of formula V in a suitable solvent. Examples of suitable solvents include: ethers such as dietyhl ether, dioxane and tetrahydrofuran; halogenated hydrocarbons, such as chloroform and dichloromethane; aromatic hydrocarbons, such as benzene and toluene; and dimethylformamide. The reaction can be carried out in the presence of an aromatic or tertiary amine such as pyridine or triethylamine, in which case the amine itself can be used as solvent. The reaction is performed at a temperature between −10° C. and that of the boiling point of the solvent, during a period of time from 6 h to 5 days.

The compounds of formula I may be transformed into their corresponding acid addition salts following standard procedures, for example by treatment with an acid such as hydrochloric acid, sulphuric acid, nitric acid, oxalic acid or methanesulfonic acid.

Amines of formulae III and V can be prepared according to the procedures described in our patent applications EP 441226 and EP 528172.

Acids of general formula II can be obtained by reaction of a 2-chloromethylquinoline derivative hydrochloride of formula VII with an ester of formula VI (wherein R means methyl or ethyl) in the presence of a base such as potassium carbonate in a suitable solvent such as dimethylformamide, at a temperature between room temperature and 80° C. during a period of time from 1 to 24 h; followed by hydrolisis of the intermediate ester thus obtained by treatment with potassium carbonate in a suitable solvent such as methanol-water mixtures, at the temperature of the boiling point of the solvent and during a period of time from 30 min. to 12 h.

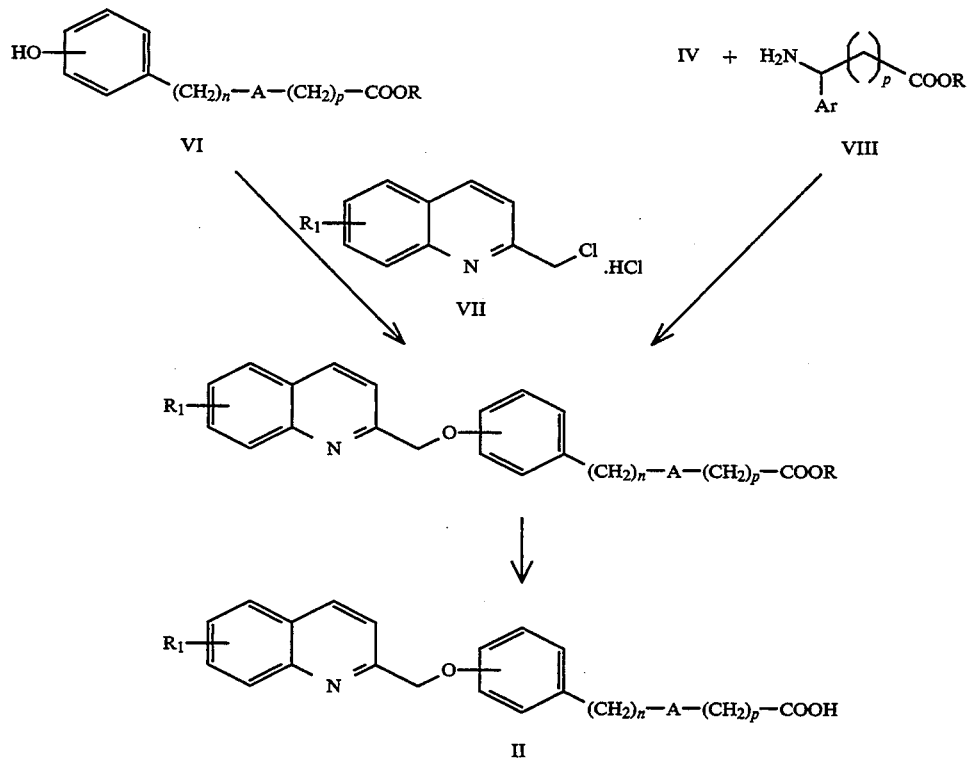

Alternatively, compounds of formula II wherein A represents a group of formula —CONHCH(Ar-)—, —SO$_2$NHCH(Ar)—, —OCONHCH(Ar)— or —NHCONHCH(Ar)— can also be prepared by reaction of a compound of formula IV with a compound of formula VIII (wherein Ar, p and R have the previously defined meaning) in the same experimental conditions mentioned above for the reaction of IV with V, to give an intermediate ester which is then converted to a compound of formula II following the procedure described above.

Compounds of formula IV are prepared by a similar sequence to that described for the preparation of II which involves as first step reacting a 2-chloromethylquinoline derivative hydrochloride of formula VII with a compound of formula IX (wherein n has the previously defined meaning and Q' represents —COOR, —OP or —NHP', where R is as above defined and P and P' are hydroxy- and amino-protecting groups; examples of the protecting agents and their addition and removal are generally known in the art) in the same experimental conditions mentioned above for the reaction of VI with VII, to give a compound of formula X. When in the starting product of formula IX Q' represents —COOR, the corresponding compound of formula IV (wherein Q represents —COOH) is obtained from a compound of formula X following an analogous procedure to that described for the preparation of II. Compounds of formula IV wherein Q represents —COCl are prepared from compounds of formula IV wherein Q represents —COOH following conventional procedures which are well known to those skilled in organic synthesis, for example by treatment of the acid with thionyl chloride or oxalyl chloride. When in a compound of formula IX Q' represents —OP or —NHP', the reaction of VII with IX leads to a compound of formula X, which is converted to a compound of formula IV in two steps: removal of the protecting groups following conventional procedures, which are well known to those skilled in the art and which will depend on the nature of the protecting group employed; and transformation of the resulting hydroxy or amino group into a group Q (—OC(=O)G$_1$ and —NHC(=O)OPh, respectively) by treatment with phenyl chloroformate under standard conditions.

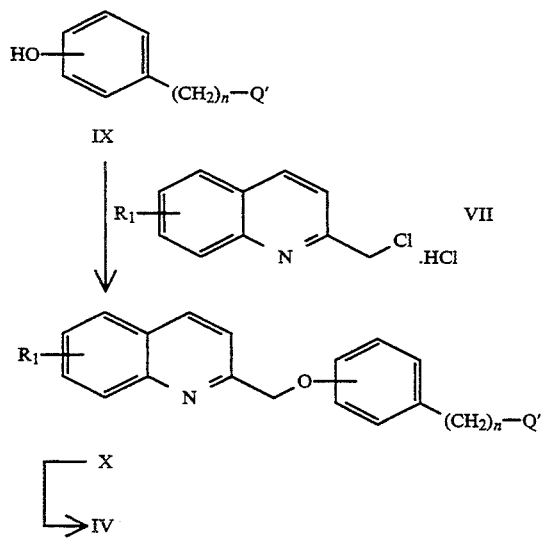

Compounds of formulae VI, VII, VIII and IX are either commercially available, or widely described in the literature or can be prepared by methods similar to those described, starting from commercially available products.

The compounds of the present invention possess the capacity to both antagonize PAF and inhibit 5-lipoxygenase enzyme. Therefore, they are useful in the treatment of diseases where PAF and/or 5-lipoxygenase are involved. Being potent PAF antagonists, they are useful as preventive and therapeutic drugs for the treatment of circulatory diseases caused by PAF, such as thrombosis, cerebral apoplexy (e.g. cerebral hemorrhage, cerebral thrombosis), myocardial infarction, angina pectoris, thrombotic phlebitis, trombocytopenic purpura; nephritis (e.g. glomerular nephritis), diabetic nephrosis, pancreatitis; shock states (e.g. septic shock observed after severe infection or postoperatively, intravascular agglutination syndrome caused by endotoxin, anaphylactic shock, hemorrhagic shock, myocardial ischemia); gastrointestinal tract diseases where PAF is involved (e.g. gastric ulcer, inflammatory bowel disease); asthma and other diseases related to allergy and inflammation (e.g. dermatitis, urticaria, arthritis, psoriasis); pneumonia; rejection due to increased PAF production after implantation of organs; and postoperative organodysfunctions (e.g. in heart, liver and kidney). They can also be used for contraception of female mammals by supressing cell division and/or ovoimplantation on the uterus, in the treatment of endometriosis and in the prevention or treatment of hyperendothelinemia induced by excess secretion of endothelin. Being 5-lipoxygenase enzyme inhibitors and, therefore, inhibitors of leukotriene biosynthesis, they are useful as preventive and therapeutic agents for the treatment of diseases such as asthma, allergy- and inflammation-related disorders (e.g. rhinitis, dermatitis, urticaria, eczema, psoriasis), rheumatoid arthritis, gout and inflammatory bowel disease. Having a dual activity as PAF antagonists and 5-lipoxygenase inhibitors, they are particularly useful for the treatment or prevention of complex pathologies such as asthma and other diseases related to allergy and inflammation (e.g. dermatitis, urticaria, arthritis, psoriasis), inflammatory bowel disease, and ischemia and shock states (e.g. septic shock observed after severe infection or postoperatively, intravascular agglutination syndrome caused by endotoxin, anaphylactic shock, hemorrhagic shock, myocardial ischemia) where several mediators are involved, such as PAF and leukotrienes.

The following pharmacological tests explain the activity of the compounds of the present invention in more detail.

PHARMACOLOGICAL TEST 1

Inhibition of platelet aggregation induced by PAF.

Blood is obtained by cardiac puncture of male New Zealand albino rabbits (b.w. 2–2.5 Kg) and coagulation is prevented by adding 1 part of 3.16% sodium citrate dihydrate in 9 parts of blood. Platelet rich plasma (PRP) is prepared by centrifuging the blood at 250×g for 10 min. at 4° C. and then it is diluted with platelet poor plasma (PPP) obtained by further centrifuging at 3000×g for 10 min. The platelet count is adjusted to $3\times10^5/mm^3$. Platelet aggregation induced by PAF ($C_{18}$, prepared in our laboratory) (15 nM) is determined by the Born nephelometric technique (J. Physiol., 1962, 162, 67) using an aggregometer Chrono-log 500. The activities of the inhibitors are expressed as the IC$_{50}$ value, that is to say the concentration of the drug needed to inhibit platelet aggregation by 50%. The results are shown in table I below.

TABLE I

| Compound No. | IC$_{50}$ (μM) |
| --- | --- |
| 1 | 6.7 |
| 2 | 1.8 |
| 3 | 0.080 |
| 4 | 0.012 |
| 5 | 0.68 |
| 6 | 0.74 |
| 7 | 0.055 |

TABLE I-continued

| Compound No. | IC$_{50}$ (μM) |
|---|---|
| 10 | 0.55 |
| 13 | 0.66 |

PHARMACOLOGICAL TEST 2

Inhibition of the hypotensive effect induced by PAF in normotense rats.

Male Sprage Dawley rats (b.w. 180–220 g) anaesthetized with sodium pentobarbital (50 mg/Kg, i.p. 1 mL/100 g) are used. In order to measure the arterial pressure, a polyethylene catheter is introduced into the carotid artery. The arterial pressure is recorded with the help of a transducer coupled to a R611 Beckman polygraph. The test compounds are administered through the femoral vein 3 min. before PAF injection (0.5 mcg/Kg, i.v.). Control animals receive only the vehicle. Table II shows the inhibition of PAF-induced hypotension of the different compounds, expressed as the ID$_{50}$ value, that is to say, the amount of compound by weight of animal (dose) needed to inhibit PAF-induced hypotension by 50%.

TABLE II

| Compound No. | ID$_{50}$ (mg/Kg i.v.) |
|---|---|
| 1 | 0.69 |
| 2 | 0.057 |
| 3 | 0.036 |
| 4 | 0.041 |
| 5 | 0.21 |
| 6 | 0.16 |
| 7 | 0.25 |
| 10 | 0.12 |
| 13 | 0.21 |

PHARMACOLOGICAL TEST 3

Inhibition of LTB$_4$ production by human granulocytes.

Human promyelocytes (HL-60 cells) are grown in a RPMI 1640 medium suplemented with 20% heat-inactivated fetal bovine serum, 50 U/mL penicillin and 50 μg/mL streptomycin under an atmosphere of 5% CO$_2$ at 37° C. Cells are exposed to 1.3% DMSO for 5 days in order to differentiate them into mature granulocytes and then are washed and resuspended in Dubelcco's phosphate-buffered saline at $10^6$ cells/mL. HL-60 ($10^6$ cells/mL) are incubated for 15 min at 37° C. in the presence or absence (vehicle only) of test compound. Cells are then stimulated by A23187 ($5 \times 10^{-6}$M) for 15 min. LTB$_4$ secreted into the external medium is measured by EIA (enzymo immunoassay) using a commercially available LTB$_4$-EIA kit. The activities of the inhibitors are expressed as the IC$_{50}$ value.

Representative compounds of the invention were tested in this assay and were found to exhibit an IC$_{50} \leq 5$ μM.

According to the activity of the compounds disclosed, the present invention further provides compositions that comprise a compound of the present invention together with an excipient and optionally other auxiliary agents, if necessary. The compounds of the present invention can be administered in different pharmaceutical preparations, the precise nature of which will depend, as it is well known, upon the chosen route of administration and the nature of the pathology to be treated.

Thus, solid compositions according to the present invention for oral administration include compressed tablets, dispersible powders, granules and capsules. In tablets, the active component is admixed with at least one inert diluent such as lactose, starch, mannitol, microcrystalline cellulose or calcium phosphate; granulating and disintegrating agents for example corn starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a sustained action over a longer period. Gastric film-coated or enteric film-coated tablets can be made with sugar, gelatin, hydroxypropylcellulose, or acrylic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as ethoxylated saturated glycerides. Soft gelatin capsules are possible wherein the active ingredient is mixed with water or an oily medium, for example peanut oil, liquid paraffin or olive oil.

Dispersible powders and granules suitable for preparation of a suspension by the addition of water provide the active ingredient in admixture with a dispersing or wetting agent, a suspending agent, such as sodium carboxymethylcellulose, sodium alginate, polyvinylpirrolidone, gum tragacanth, xantham gum, gum acacia, and one or more preservatives, such as methyl or n-propyl-p-hydroxybenzoate. Additional excipients, for example sweetening, flavoring and coloring agents may also be present.

Liquid compositions for oral administration include emulsions, solutions, suspensions, syrups and elixirs containing commonly used inert diluents, such as distilled water, ethanol, sorbitol, glycerol, or propylene glycol. Such compositions may also comprise adjuvants such as wetting agents, suspending agents, sweetening, flavoring, perfuming, preserving agents and buffers.

Other compositions for oral administration include spray compositions, which may be prepared by known methods. The spray compositions will contain a suitable propellent.

Preparations for injection according to the present invention for parenteral administration include sterile aqueous or non-aqueous solutions, suspensions or emulsions, in a non-toxic parentally-acceptable diluent or solvent. Examples of aqueous solvents or suspending media are distilled water for injection, Ringer's solution, and isotonic sodium chloride solution. Examples of non-aqueous solvents or suspending media are propylene glycol, polyethylene glycol, vegetable oils such as olive oil, or alcohols such as ethanol. These compositions may also include adjuvants such as wetting, preserving, emulsifying and dispersing agents. They may be sterilized by one of the known methods or manufactured in the form of sterile solid compositions which can be dissolved in sterile water or some other sterile injectable medium immediately before use. When all of the components are sterile, the injectables will maintain the sterility if they are manufactured in sterile environment.

A compound of the invention may also administered in the form of suppositories or enemas (which include aqueous or oily solutions as well as suspensions and emulsions) for rectal administration of the drug, or as creams, ointments, pastes, lotions, gels, sprays, foams, aerosols, solutions, suspensions or powders for topical use. Such compositions are prepared following conventional procedures, well known to those skilled in the art.

The dosage and frequency of dose may vary depending upon symptoms, age and body weight of the patient, as well as upon the route of administration. In general, the compounds of the invention may be administered orally or parenterally to human patients in a daily dose from 5 to 5000 mg for an adult, preferably a dosage from 25 to 1000 mg, which may be administered either as a single dose or as divided doses. A preferred dosage for human patients is from 0.1 to 50 mg/kg of body weight, more preferably from 0.5 to 10 mg/kg of body weight. However, in particular cases, at the discretion of the attending physician, doses outside the broader range may be required.

The compositions for topical administration will contain 0.5–10% by weight of a compound of formula I.

Following are some representative preparations for tablets, capsules, syrups, aerosols, injectables and creams. They can be prepared following standard procedures and they are useful in the treatment of PAF- and/or 5-lipoxygenase- mediated conditions and for inhibiting the activity of PAF and/or 5-lipoxygenase in a mammal (including humans) in need thereof.

| Tablets | |
| --- | --- |
| Compound of formula I | 100 mg |
| Dibasic calcium phosphate | 125 mg |
| Sodium starch glycolate | 10 mg |
| Talc | 12.5 mg |
| Magnesium stearate | 2.5 mg |
| | 250.0 mg |
| Hard gelatin capsules | |
| Compound of formula I | 100 mg |
| Lactose | 197 mg |
| Magnesium stearate | 3 mg |
| | 300 mg |
| Syrup | |
| Compound of formula 1 | 0.4 g |
| Sucrose | 45 g |
| Flavouring agent | 0.2 g |
| Sweetening agent | 0.1 g |
| Water to | 100 mL |
| Aerosol | |
| Compound of formula I | 4 g |
| Flavouring agent | 0.2 g |
| Propylene glycol to | 100 ml |
| Suitable propellent to | 1 unit |
| Injectable preparation | |
| Compound of formula I | 100 mg |
| Benzylic alcohol | 0.05 ml |
| Propylene glycol | 1 ml |
| Water to | 5 ml |
| Cream | |
| Compound of formula I | 2 g |
| Dimethyl acetamide | 2 g |
| White paraffin | 25 g |
| Stearic alcohol | 22 g |
| Propylene glycol | 12 g |
| Sodium lauryl sulfate | 1.5 g |
| Methylparabene | 0.3 g |
| Purified water | 31.6 g |

The following examples illustrate, but do not limit, the scope of the present invention.

REFERENCE EXAMPLE 1

Methyl p-(2-quinolylmethoxy)phenylacetate

To a mixture of 2-(chloromethyl)quinoline hydrochloride (1 g, 4.6 mmol) and methyl p-hydroxyphenylacetate (0.83 g, 5 mmol) in anhydrous dimethylformamide (20 mL), was added potassium carbonate (2.33 g) and the mixture was heated at 60° C. for 8 h. Dimethylformamide was removed, and the residue was partitioned between water and chloroform. The organic phase was dried over sodium sulfate and the solvent was removed, to afford 1.68 g of a crude product that was purified by chromatography on silica gel (ethyl acetate-hexane 1:1), to give 1.2 g of the title compound (yield: 84%).

IR (film) $\nu$: 3024, 2945, 1730, 1595, 1503, 1423, 1242, 1217, 1158, 1050, 826 cm$^{-1}$. $^1$H NMR (80 MHz, CDCl$_3$) $\delta$ (TMS): 8.18 (s, 1H, Ar), 8.04 (s, 1H, Ar), 7.8–7.4 (m, 4H, Ar), 7.2–6.9 (m, 4H, Ar), 5.34 (s, 2H, CH$_2$O), 3.64 (s, 3H, CH$_3$), 3.53 (s, 2H, CH$_2$CO).

REFERENCE EXAMPLE 2 p-(2-Quinolylmethoxy)phenylacetic acid

To a solution of the compound obtained in reference example 1 (1.2 g, 3.9 mmol) in methanol (25 mL) was added potassium carbonate (1.23 g) dissolved in water (12.5 mL) and the mixture was heated at reflux for 1 h. Next, methanol was removed, more water was added and the resulting solution was extracted with diethyl ether. The aqueous phase was cooled in an ice bath and acidified with 5N HCl. The solid thus precipitated was filtered and dried to give 0.7 g of the title compound (yield: 61%).

IR (film) $\nu$: 3200–2400, 1699, 1594, 1499, 1286, 1243, 1223, 1139, 1071, 827, 802 cm$^{-1}$; $^1$H NMR (80 MHz, CDCl$_3$+CD$_3$OD) $\delta$ (TMS): 8.3–6.9 (complex signal, 10H, Ar), 5.36 (s, 2H, CH$_2$O), 3.54 (s, 2H, CH$_2$CO).

REFERENCE EXAMPLE 3

4-(2-Quinolylmethoxy)benzophenone

Following the procedure described in reference example 1, but using 4-hydroxybenzophenone instead of methyl p-hydroxyphenylacetate, a crude product was obtained that was used in the next step without further purification.

IR (film) $\nu$: 3053, 1642, 1593, 1570, 1498, 1313, 1278, 1248, 1170, 1147 cm$^{-1}$; $^1$H NMR (80 MHz, CDCl$_3$) $\delta$ (TMS): 8.3–7.0 (complex signal, 15H, Ar), 5.47 (s, 2H, CH$_2$O).

REFERENCE EXAMPLE 4

N-[phenyl[p-(2-quinolylmethoxy)]phenylmethyl-]aminoacetic acid

To a solution of the compound obtained in reference example 3 (2 g, 5.9 mmol) in methanol (25 mL) and tetrahydrofuran (6 mL), was added at 80° C. a solution of glycine (0.44 g) in water (2 mL). Next, sodium cyanoborohydride (0.55 g) was carefully added and the resulting mixture was heated at 100° C. for 18 h. Methanol was evaporated and then water was added. The resulting solution was basified and extracted with diethyl ether. Finally, the aqueous phase was acidified to pH=7 and extracted with chloroform. The organic phase was dried and the solvents were removed, to afford 1.11 g of the title compound (yield: 47%).

IR(KBr) ν: 3200–2200, 1642, 1593, 1502, 1378, 1246, 1178, 826, 751, 699 cm⁻¹; ¹H NMR (80 MHz, CDCl₃+CD₃OD) δ (TMS): 8.4–7.0 (complex signal, 15H, Ar), 5.47 (s, 1H, CH), 5.36 (s, 2H, CH₂O), 3.38 (s, 2H, CH₂CO).

REFERENCE EXAMPLE 5

Methyl 3-hydroxyphenylacetate

To a solution of 3-hydroxyphenylacetic acid (2 g, 13.2 mmol) in methanol (45 mL) was added concentrated H₂SO₄ (0.82 mL) and the mixture was heated at reflux for 18 h. Next, the solvent was removed and the residue was diluted with water and extracted with ethyl acetate. The organic phase was dried over anhydrous sodium sulfate and the solvent was removed, to yield 1.54 g of the desired compound (yield: 71%).

IR (film) ν: 3600–2400, 1711, 1586, 1449, 1433, 1276, 1154, 1012, 773, 690 cm¹; ¹H NMR (80 MHz, CDCl₃+CD₃OD) δ (TMS): 7.4–6.6 (complex signal, 4H, Ar), 3.69 (s, 3H, CH₃), 3.60 (s, 2H, CH₂).

REFERENCE EXAMPLE 6

Methyl 3-(2-quinolylmethoxy)phenylacetate

Following the procedure described in reference example 1, but using the compound obtained in reference example 5 instead of methyl p-hydroxyphenylacetate, the title compound was obtained in 19% yield.

IR (film) ν: 3052, 2944, 1730, 1594, 1581, 1485, 1444, 1427, 1260, 1151 cm⁻¹; ¹H NMR (80 MHz, CDCl₃) δ (TMS): 8.17 (m, 1H, Ar), 8.06 (m, 1H, Ar), 7.8–7.4 (m, 4H, Ar), 7.2–6.8 (m, 4H, Ar), 5.36 (s, 2H, CH₂O), 3.63 (s, 3H, CH₃), 3.57 (s, 2H, CH₂CO).

REFERENCE EXAMPLE 7

3-(2-Quinolylmethoxy)phenylacetic acid

Following the procedure described in reference example 2, but starting from the compound obtained in reference example 6, the title compound of this example was obtained.

IR (film) ν: 3200–2300, 1710, 1592, 1426, 1316, 1284, 1262, 1242, 1131, 1062, 826, 771, 740 cm⁻¹. ¹H NMR (80 MHz, CDCl₃) δ (TMS): 9.36 (broad s., COOH), 8.14 (m, 2H, Ar), 7.9–7.4 (m, 4H, Ar), 7.3–6.8 (m, 4H, Ar), 5.40 (s, 2H, CH₂O), 3.62 (s, 2H, CH₂CO).

REFERENCE EXAMPLE 8

Methyl p-(2-quinolylmethoxy)benzoate

Following the procedure described in reference example 1, but using methyl p-hydroxybenzoate instead of methyl p-hydroxyphenylacetate, a crude product was obtained that was directly used in the next step as obtained.

¹H NMR (80 MHz, CDCl₃) δ (TMS): 8.3–6.9 (complex signal, 10H, Ar), 5.43 (s, 2H, CH₂O), 3.87 (s, 3H, CH₃).

REFERENCE EXAMPLE 9 p-(2-Quinolylmethoxy)benzoic acid

Following the procedure described in reference example 2, but starting from the compound obtained in reference example 8, the title compound of this example was obtained (yield: 47%).

mp:>300° C.; IR (film) ν: 3439, 3058, 1705, 1599, 1502, 1377, 1249, 1171, 1106, 1037, 775 cm⁻¹; ¹H NMR (80 MHz, DMSO-d₆) δ (TMS): 8.40 (d, J=8.4 Hz, 1H, Ar), 8.1–7.6 (m, 7H, Ar), 7.05 (m, 2H, Ar), 5.43 (s, 2H, CH₂O).

REFERENCE EXAMPLE 10

Methyl 3-hydroxybenzoate

Following the procedure described in reference example 5, but starting from 3-hydroxybenzoic acid, the title compound of this example was obtained (quantitative yield).

IR (film) ν: 3600–3200, 2947, 1694, 1585, 1447, 1433, 1296, 1230, 1103, 997, 755 cm⁻¹; ¹H NMR (80 MHz, CDCl₃) δ (TMS): 7.7–7.0 (complex signal, 4H, Ar), 6.14 (broad s., OH), 3.91 (s, 3H, CH₃).

REFERENCE EXAMPLE 11

Methyl 3-(2-quinolylmethoxy)benzoate

Following the procedure described in reference example 1, but using the compound obtained in reference example 10 instead of methyl p-hydroxyphenylacetate, the title compound of the example was obtained.

IR (film) ν: 3054, 2944, 1713, 1669, 1593, 1580, 1440, 1287, 1216, 1089 cm⁻¹; ¹H NMR (80 MHz, CDCl₃) δ (TMS): 8.3–7.2 (complex signal, 10H, Ar), 5.41 (s, 2H, CH₂O), 3.89 (s, 3H, CH₃).

REFERENCE EXAMPLE 12

3-(2-Quinolylmethoxy)benzoic acid

Following the procedure described in reference example 2, but starting from the compound obtained in reference example 11, the title compound was obtained in 49% yield.

mp: 178°–182° C.; IR (film) ν: 3200–2300, 1699, 1591, 1485, 1320, 1285, 1268, 1234, 1218, 1202, 1073, 831, 770, 752 cm⁻¹; ¹H NMR (80 MHz, CDCl₃+CD₃OD) δ (TMS): 8.4–7.2 (complex signal, 10H, Ar), 5.41 (s, 2H, CH₂O).

REFERENCE EXAMPLE 13

N-(tert-butoxycarbonyl)-D-2-phenylglycine

To a cooled (ice bath) solution of D-2-phenylglycine (15 g, 99.2 mmol) in water (104 mL) and tetrahydrofuran (104 mL), was added 1N NaOH (104 mL). Keeping the flask in the ice bath, di-tert-butyl dicarbonate was added (22.75 g) and the reaction mixture was stirred at room temperature for 2 h. Tetrahydrofuran was evaporated and the resulting solution was extracted with chloroform at basic pH. After acidifying with 5N HCl and filtering the solid precipitated, 17.77 g of the title product was obtained as a white solid (yield: 71%).

IR (film) ν: 3200–2300, 1699, 1591, 1485, 1320, 1285, 1268, 1234, 1218, 1202, 1073, 831, 770, 752 cm⁻¹; ¹H NMR (80 MHz, DMSO-d₆) δ (TMS): 7.33 (s, 5H, Ar), 5.06 (d, J =8.2 Hz, 1H, CH), 1.37 (s, 9H, CH₃(BOC)).

REFERENCE EXAMPLE 14

1-[N-(tert-butoxycarbonyl)-D-2-phenylglycinyl]-4-(3-pyridylcyanomethyl)piperidine To a mixture of the compound obtained in reference example 13 (7.5 g, 29.8 mmol), 4-(3-pyridylcyanomethyl)piperidine (6 g, 29.8 mmol) (obtained according to the procedure described in EP 441226) and 1-hydroxybenzotriazole (4 g) in anhydrous dimethylformamide (250 mL), was added at 0° C. dicyclohexylcarbodiimide (6.14 g) and the resulting solution was stirred at room temperature overnight. The white solid formed was filtered, the solvent was removed under vacuum and the resulting residue was dissolved in ethyl acetate. The organic solution was washed with saturated solution of sodium bicarbonate (2x), dried over sodium sulfate and evaporated, to afford 14.5 g of a residue that was purified by chromatography on silica gel (ethyl acetate). 11.2 g of the title compound was obtained (yield: 86%).

IR (film) $\nu$: 3399, 2967, 2925, 2238, 1694, 1631, 1444, 1365, 1244, 1166, 1048, 879, 713 cm$^{-1}$; $^1$H NMR (80 MHz, CDCl$_3$) $\delta$ (TMS): 8.7–8.3 (m, 2H, pir), 7.55 (broad d, J =7.9 Hz, 1H, pyr), 7.33 (s, 6H, Ar+pyr), 6.06 (d, J=7.6 Hz, 1H, NH), 5.53 (d, J=7.6 Hz, 1H, CHNH), 4.70 (m, 1H, pip), 4.0–3.4 (m), 3.1–1.5 (complex signal), 1.40 (s, 9H, CH$_3$(BOC)).

REFERENCE EXAMPLE 15

1-(D-2-phenylglycinyl)-4-(3-pyridylcyanomethyl)-piperidine

To a solution of the compound obtained in reference example 14 (11.1 g, 25.5 mmol) in chloroform (150 mL), cooled to 0° C., was added dropwise 56.5 mL of a 6.2N dioxane/HCl solution. When the addition was complete, the mixture was stirred at room temperature for 2 h and the solvents were removed. At 0° C., cold 2N NaOH solution was added until basic pH and the mixture was extracted three times with chloroform. The organic phase was separated, dried over sodium sulfate and the solvents were removed, to afford 10.16 g of the title compound.

IR (film) $\nu$: 3600–3100, 2997, 2912, 2237, 1635, 1445, 1422, 1251, 1118, 872, 757, 714 cm$^{-1}$; $^1$H NMR (80 MHz, CDCl$_3$) $\delta$ (TMS): 8.58 (dd, J$_a$=4.6 Hz, J$_b$=1.5 Hz, 1H, pyr), 8.43 (m, 1H, pyr), 7.53 (m, 1H, pyr), 7.29 (s, 6H, Ar+pyr), 4.70 (broad s, 2H, pip+CHNH$_2$), 4.0–3.5 (m, 2H), 3.1–2.2 (m, 2H, pip), 2.05 (s, 2H, NH$_2$), 2.0–1.1 (m, 5H, pip).

REFERENCE EXAMPLE 16

1-[3-[N-(tert-butoxycarbonyl)amino]-3-phenylpropionyl]-4-(3-pyridylcyanomethyl)piperidine Following the procedure described in reference example 14, but using 3-[N-(tert-butoxycarbonyl)amino]-3-phenylpropionic acid (obtained according to the procedure described in EP 528172) instead of the compound obtained in reference example 13, the title compound was obtained (yield: 85%).

IR (film) $\nu$: 3361, 2971, 2926, 2237, 1701, 1663, 1624, 1446, 1422, 1385, 1363, 1245, 1166, 1045, 702 cm$^{-1}$; $^1$H NMR (80 MHz, CDCl$_3$) $\delta$ (TMS): 8.56 (m, 2H, pyr), 7.66 (m, 1H, pyr), 7.39 (m, 1H, pyr), 7.28 (s, 5H, Ar), 6.22 (m, 1H, NH), 5.04 (m, 1H, CHNH), 4.60 (m, 1H, pip), 3.69 (m, 2H), 2.89 (d, J=6.4 Hz, 2H, CH$_2$CO), 2.7–1.5 (complex signal, pip), 1.39 (s, 9H, CH$_3$(BOC)).

REFERENCE EXAMPLE 17

1-(3-amino-3-phenylpropionyl)-4-(3-pyridylcyanomethyl)piperidine

Following the procedure described in reference example 15, but starting from the compound obtained in reference example 16, the title compound was obtained.

IR (film) $\nu$: 3600–3100, 2933, 2849, 2237, 1663, 1624, 1446, 1422, 1118, 872, 753, 703 cm$^{-1}$; $^1$H NMR (80 MHz, CDCl$_3$) $\delta$ (TMS): 8.57 (m, 2H, pyr), 7.65 (m, 1H, pyr), 7.32 (broad s, 6H, Ar+pyr), 4.9–4.6 (m, 1H, pip), 4.49 (t, J=6.4 Hz, 1H, CHCH$_2$), 4.0–3.6 (m), 3.1–2.7 (m), 2.60 (d, J=6.4 Hz, 2H, CHCH$_2$), 1.92 (s, 2H, NH$_2$), 2.5–1.0 (complex signal, 5H).

REFERENCE EXAMPLE 18 p-(2-Quinolylmethoxy)benzoyl chloride, hydrochloride

To a solution of the acid obtained in reference example 9 (23.8 g, 85.2 mmol) in dichloromethane (300 mL), was added oxalyl chloride (30 mL) and the mixture was stirred at room temperature for 2 h. The solvent was removed, to afford a crude product that was directly used in the next step as obtained.

IR (film) $\nu$: 3437, 3031, 2910, 2280, 1957, 1759, 1736, 1592, 1570, 1496, 1257, 1161, 871, 825 cm$^{-1}$;

EXAMPLE 1

1-[p-(2-Quinolylmethoxy)phenylacetyl]-4-[(2-methyl-3-pyridyl)cyanomethyl]piperazine To a mixture of the acid obtained in reference example 2 (0.7 g, 2.3 mmol), 1-[(2-methyl-3-pyridyl)-cyanomethyl]piperazine (0.5 g, 2.3 mmol) (obtained according to the procedure described in EP 528172) and 1-hydroxybenzotriazole (0.38 g, 2.4 mmol) in anhydrous dimethylformamide (20 mL), was added at 0° C. and under a nitrogen atmosphere dicyclohexylcarbodiimide (0.48 g, 2.3 mmol) and the reaction mixture was stirred at room temperature for 18 h. The solvents were removed under vacuum, the resulting residue was stirred with ethyl acetate and the white solid formed was filtered. The organic solution was washed with saturated solution of sodium bicarbonate, with water and finally with brine, dried over sodium sulfate and the solvents were removed, to afford 1.27 g of a residue that was purified by chromatography on silica gel (ethyl acetate: methanol 3%). 643 mg of the title compound of the example was obtained (yield: 57%).

mp: 64°–68° C.; IR (film) $\nu$: 3051, 2912, 2816, 1635, 1503, 1436, 1240, 1225, 998, 824 cm$^{-1}$; $^1$H NMR (80 MHz, CDCl$_3$) $\delta$ (TMS): 8.53 (d, J=4.7 Hz, 1H, Ar), 8.14 (m, 2H, Ar), 7.9–6.9 (complex signal, 10H, Ar), 5.37 (s, 2H, CH$_2$O), 4.85 (s, 1H, CHCN), 3.66 (s, 2H, CH$_2$CO), 3.43 (m, 4H, pip), 2.61 (s, 3H, CH$_3$), 2.45 (m, 4H, pip).

EXAMPLE 2

1-[N-[p-(2-quinolylmethoxy)phenylphenylmethyl]aminoacetyl]-4-[(2-methyl-3-pyridyl)cyanomethyl]piperazine Following the procedure described in example 1, but using the acid obtained in reference example 4, the title compound of the example was obtained (yield: 21%).

mp: 79°–83° C.; IR (film) $\nu$: 3312, 3050, 2912, 2818, 1642, 1602, 1498, 1434, 1237, 997, 823 cm$^{-1}$; $^1$H NMR (80 MHz, CDCl$_3$) $\delta$ (TMS): 8.53 (broad d, J=3.5 Hz, 1H, Ar), 8.11 (m, 2H, Ar), 7.9–6.9 (complex signal, 15H, Ar), 5.34 (s, 2H, CH$_2$O), 4.87 (s, 1H), 4.78 (s, 1H), 3.61 (m, 4H, pip), 3.34 (s, 2H, CH$_2$CO), 2.61 (s, 3H, CH$_3$), 2.56 (m, 4H, pip), 2.15 (broad s., NH).

EXAMPLE 3

1-[3-[N-[p-(2-quinolylmethoxy)phenylacetyl]]amino-3-phenylpropionyl]-4-[(2-methyl-3-pyridiyl)cyanomethyl]piperazine Following a similar procedure to that described in example 1, but starting from the acid obtained in reference example 2 and 1-(3-amino-3-phenylpropionyl)-4-[(2-methyl-3-pyridyl)cyanomethyl]piperazine (obtained according to the procedure described in EP 528172), the title compound of the example was obtained (yield: 43%).

mp: 89°–92° C.; IR (film) ν: 3291, 3051, 2917, 1641, 1502, 1434, 1298, 1238, 1174, 1141, 997, 823, 752, 699 cm$^{-1}$; $^1$H NMR (80 MHz, CDCl$_3$) δ (TMS): 8.51 (dd, $J_a$=4.8 Hz, $J_b$=1.5 Hz, 1H, Ar), 8.11 (m, 2H, Ar), 7.9–6.9 (complex signal, 16H, 15H Ar+NH), 5.36 (s, 2H, CH$_2$O), 5.30 (m, 1H, CHNH), 4.80 (s, 1H, CHCN), 3.50 (s, 2H, CH$_2$CONH), 3.21 (m, 4H, pip), 2.90 (d, J=5.2 Hz, 1H, CHCH$_2$CO), 2.72 (d, J=5.2 Hz, 1H, CHCH$_2$CO), 2.57 (s, 3H, CH$_3$), 2.29 (m, 4H, pip).

EXAMPLE 4

1-[3-[N-[3-(2-quinolylmethoxy)phenylacetyl]]amino-3-phenylpropionyl]-4-[(2-methyl-3-pyridyl)cyanomethyl]piperazine Following the procedure described in example 3, but using the acid obtained in reference example 7 instead of the acid obtained in reference example 2, the title compound of the example was obtained (yield: 47%).

mp: 83°–86° C.; IR (film) ν: 3289, 3049, 2913, 1641, 1484, 1438, 1249, 1144, 997, 773, 699 cm$^{-1}$; $^1$H NMR (80 MHz, CDCl$_3$) δ (TMS): 8.51 (d, J=4.7 Hz, 1H, Ar), 8.12 (m, 2H, Ar), 7.9–6.8 (complex signal, 16H, 15H Ar+NH), 5.37 (s, 2H, CH$_2$O), 5.32 (m, 1H, CHNH), 4.79 (s, 1H, CHCN), 3.55 (s, 2H, CH$_2$CONH), 3.5–3.1 (m, 4H, pip), 2.89 (d, J=5.1 Hz, 1H, CHCH$_2$CO), 2.71 (d, J=5.1 Hz, 1H, CHCH$_2$CO), 2.57 (s, 3H, CH$_3$), 2.34 (m, 4H, pip).

EXAMPLE 5

1-[3-[N-[p-(2-quinolylmethoxy)benzoyl]]amino-3-phenylpropionyl]-4-[(2-methyl-3-pyridyl)cyanomethyl]piperazine Following the procedure described in example 3, but using the acid obtained in reference example 9 instead of the acid obtained in reference example 2, the title compound of the example was obtained (yield: 21%).

mp: 104°–110° C.; IR (film) ν: 3330, 3051, 2913, 2818, 1631, 1599, 1492, 1435, 1299, 1244, 1174, 997, 843, 822, 766, 699 cm$^{-1}$; $^1$H NMR (80 MHz, CDCl$_3$) δ (TMS): 8.51 (broad d, J=4.8 Hz, 1H, Ar), 8.4–7.0 (complex signal, 18H, 17H Ar+NH), 5.57 (m, 1H, CHNH), 5.43 (s, 2H, CH$_2$O), 4.82 (s, 1H, CHCN), 3.5–3.1 (m, 4H, pip), 3.05 (d, J=5.1 Hz, 1H, CH$_2$CO), 2.85 (d, J=5.1 Hz, 1H, CH$_2$CO), 2.59 (s, 3H, CH$_3$), 2.39 (m, 2H, pip), 2.07 (m, 2H, pip).

EXAMPLE 6

1-[3-[N-[3-(2-quinolylmethoxy)benzoyl]]amino-3-phenylpropionyl]-4-[(2-methyl-3-pyridyl)cyanomethyl]piperazine Following the procedure described in example 3, but using the acid obtained in reference example 12 instead of the acid obtained in reference example 2, the title compound of the example was obtained (yield: 61%).

mp: 101°–104° C.; IR(KBr) ν: 3320, 3052, 2912, 2818, 1641, 1573, 1501, 1434, 1297, 1222, 1126, 997, 823, 751, 699 cm$^{-1}$; $^1$H NMR (80 MHz, CDCl$_3$) δ (TMS): 8.52 (dd, $J_a$=4.8 Hz, $J_b$=1.5 Hz, 1H, Ar), 8.5–7.1 (complex signal, 18H, 17H Ar+NH), 5.54 (m, 1H, CHNH), 5.42 (s, 2H, CH$_2$O), 4.83 (s, ½H, CHCN), 4.80 (s, ½H, CHCN), 3.22 (m, 4H, pip), 3.06 (d, J=5.3 Hz, 1H, CH$_2$CO), 2.86 (d, J=5.3 Hz, 1H, CH$_2$CO), 2.65 (s, 3H, CH$_3$), 2.5–2.1 (m, 4H, pip).

EXAMPLE 7

1-[3-[N-[p-(2-quinolylmethoxy)benzoyl]]amino-3-phenylpropionyl]-4-(3-pyridylcyanomethyl)piperidine To a solution of the compound obtained in reference example 17 as the dihydrochloride (10 g, 23.7 mmol) in chloroform (300 mL), was added triethylamine (13.23 mL). The resulting mixture was cooled in an ice bath, the compound obtained in reference example 18 was added and the reaction mixture was stirred at room temperature for 3 h. The resulting solution was diluted with chloroform, 0.5N HCl was added and it was extracted again. Finally, it was basified and extracted several times with chloroform. 15.2 g of a crude product was obtained that was then purified by chromatography on silica gel (ethyl acetate-methanol 3%), to give 8.2 g of the title compound of the example (57% de rend.). An analytical sample was obtained by recrystallization from ethanol.

Alternatively, the title compound of the example can be obtained following the procedure described in example 1, but starting from the acid obtained in reference example 9 and the compound obtained in reference example 17 (yield: 56%).

mp: 182°–188° C.; IR(KBr) ν: 3318, 2931, 1630, 1597, 1492, 1243 cm$^{-1}$; $^1$H NMR (80 MHz, CDCl$_3$) δ (TMS): 8.50 (m, 2H, Ar), 8.12 (t, J=8.4 Hz, 2H, Ar), 7.7–7.3 (complex signal, 16H, 15H Ar+NH), 5.55 (m, 1H, CHNH), 5.41 (s, 2H, CH$_2$O), 4.65 (m, 1H, pip), 3.8–3.3 (m, 2H), 3.3–2.0 (m, 4H), 2.0–1.0 (m, 5H).

EXAMPLE 8

1-[3-[N-[3(2-quinolylmethoxy)benzoyl]]amino-3-phenylpropionyl]-4-(3-pyridylcyanomethyl)piperidine Following the procedure described in example 1, but starting from the acid obtained in reference example 12 and the compound obtained in reference example 17, the title compound of the example was obtained (yield: 45%).

mp: 91°–97° C.; IR(KBr) ν: 3321, 3051, 2914, 1631, 1473, 1421 cm$^{-1}$; $^1$H NMR (80 MHz, CDCl$_3$) δ (TMS): 8.53 (m, 2H, Ar), 8.22 (t, J=8.4 Hz, 2H, Ar), 7.9–7.1 (complex signal, 16H, 15H Ar+NH), 5.50 (m, 1H, CHNH), 5.40 (s, 2H, CH$_2$O), 4.60 (m, 1H, pip), 3.9–3.3 (m, 2H), 3.4–2.0 (m, 4H), 2.0–1.0 (m, 5H).

EXAMPLE 9

1-3-[N-[p-(2-quinolylmethoxy)phenylacetyl]]amino-3-phenylpropionyl]-4-(3-pyridylcyanomethyl)piperidine Following the procedure described in example 1, but starting from the acid obtained in reference example 2 and the compound obtained in reference example 17, the title compound of the example was obtained.

mp: 80°–86° C.; IR(KBr) ν: 3285, 2931, 1631, 1502, 1421, 1238 cm$^{-1}$; $^1$H NMR (80 MHz, CDCl$_3$) δ (TMS): 8.55 (m, 2H, Ar), 8.11 (t, J=8.4 Hz, 2H, Ar), 7.9–7.1 (complex signal, 16H, 15H Ar+NH), 5.35 (s, 2H, CH$_2$O), 5.30 (m, 1H, CHNH), 4.46 (m, 1H, pip), 3.8–3.4 (m, 2H), 3.49 (s, 2H, CH$_2$CO), 3.3–2.0 (m, 4H), 2.0–1.0 (m, 5H).

EXAMPLE 10

1-[N-[p-(2-quinolylmethoxy)phenylacetyl]-D-2-phenylglycinyl]-4-(3-pyridylcyanomethyl)piperidine Following the procedure described in example 1, but starting from the acid obtained in reference example 2 and the compound obtained in reference example 15, the title compound of the example was obtained (yield: 38%).

mp: 92°–94° C.; IR(film) ν: 3310, 3024, 2929, 2855, 2237, 1633, 1502, 1445, 1421, 1239, 824, 713, 700 cm⁻¹; $^1$H NMR (80 MHz, CDCl$_3$) δ (TMS): 8.57 (broad d, J=4.3 Hz, 1H, Ar), 8.45 (m, 1H, Ar), 8.11 (t, J=8.3 Hz, 2H, Ar), 7.9–6.8 (complex signal, 16H, 15H Ar+NH), 5.80 (broad d, J=7 Hz, 1H, CHNH), 5.34 (s, 2H, CH$_2$O), 4.67 (m, 1H, pip), 4.0–3.5 (m, 2H), 3.46 (s, 2H, CH$_2$CO), 3.1–1.0 (complex signal, 7H).

EXAMPLE 11

1-[N-[3-(2-quinolylmethoxy)phenylacetyl]-D-2-phenyl-glycinyl]-4-(3-pyridylcyanomethyl)piperidine Following the procedure described in example 1, but starting from the acid obtained in reference example 7 and the compound obtained in reference example 15, the title compound of the example was obtained (yield: 32%).

mp: 107°–109° C.; IR(film) ν: 3310, 3024, 2929, 2855, 2237, 1633, 1502, 1445, 1421, 1239, 824, 713, 700 cm⁻¹; $^1$H NMR (80 MHz, CDCl$_3$) δ (TMS): 8.7–8.3 (m, 2H, Ar), 8.11 (t, J=8.3 Hz, 2H, Ar), 7.9–6.7 (complex signal, 16H, 15H Ar+NH), 5.80 (broad d, J=6.9 Hz, 1H, CHNH), 5.31 (s, 2H, CH$_2$O), 4.67 (m, 1H, pip), 4.1–3.7 (m, 2H), 3.50 (s, 2H, CH$_2$CO), 3.1–2.2 (m, 3H), 2.0–1.0 (complex signal, 4H).

EXAMPLE 12

1-[N-[p-(2-quinolylmethoxy)benzoyl]-D-2-phenyl-glycinyl]-4-(3-pyridylcyanomethyl)piperidine Following the procedure described in example 1, but starting from the acid obtained in reference example 9 and the compound obtained in reference example 15, the title compound of the example was obtained (yield: 31%).

mp: 99°–101° C.; IR(film) ν: 3385, 2933, 1630, 1599, 1477, 1445, 1421, 1244 cm⁻¹; $^1$H NMR (80 MHz, CDCl$_3$) δ (TMS): 8.59 (d, J=4 Hz, 1H, Ar), 8.45 (m, 1H, Ar), 8.11 (t, J=8.3 Hz, 2H, Ar), 7.9–6.8 (complex signal, 16H, 15H Ar+NH), 5.98 (broad d, J=6.9 Hz, 1H, CHNH), 5.39 (s, 2H, CH$_2$O), 4.73 (m, 1H, pip), 4.3–3.4 (m, 2H), 3.3–2.3 (m, 3H), 2.2–1.2 (m, 4H).

EXAMPLE 13

1-[N-[3-(2-quinolylmethoxy)benzoyl]-D-2-phenyl-glycinyl]-4-(3-pyridylcyanomethyl)piperidine Following the procedure described in example 1, but starting from the acid obtained in reference example 12 and the compound obtained in reference example 15, the title compound of the example was obtained (yield: 25%).

mp: 93°–96° C.; IR(film) ν: 3377, 3052, 2933, 1630, 1575, 1496, 1472, 1444, 1286 cm⁻¹; $^1$H NMR (80 MHz, CDCl$_3$) δ (TMS): 8.48 (m, 2H, Ar), 8.11 (t, J=8.3 Hz, 2H, Ar), 7.9–7.1 (complex signal, 16H, 15H Ar+NH), 5.98 (broad d, J=6.8 Hz, 1H, CHNH), 5.38 (s, 2H, CH$_2$O), 4.80 (m, 1H, pip), 4.1–3.4 (m, 2H), 3.3–1.0 (complex signal, 7H).

We claim:

1. A compound of formula I:

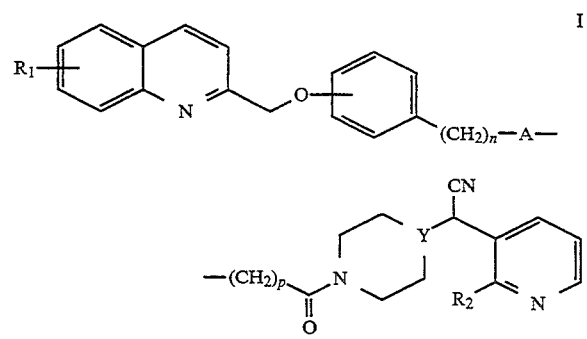

as a racemate, a diastereosiomer mixture or in optically active form wherein:
Y represents N or CH;
R$_1$ represents hydrogen, fluoro, chloro, difluoro or dichloro;
R$_2$ represents hydrogen or C$_{1-4}$ alkyl;
n is 0 or 1;
p is 0 or 1;
A represents a covalent bond or a group of formula —CONHCH(Ar)—, —NHCH(Ar)—, —SO$_2$NHCH(Ar)—, —NHCONHCH(Ar)— or —OCONHCH(Ar)—, and when p is 1, A can also represent —CH(Ar)NH—;
Ar represents phenyl or phenyl substituted with halogen, C$_{1-4}$ alkyl, C$_{1-4}$ alkoxy or trifluoromethyl;
or a pharmaceutically-acceptable salt or solvate thereof.

2. A compound according to claim 1 of formula I wherein the 2-quinolylmethoxy radical is in the para or meta position of the benzene ring and R$_1$, R$_2$, A, Y, n and p have the previously defined meaning.

3. A compound according to claim 1 of formula I wherein the 2-quinolylmethoxy radical is in the para or meta position of the benzene ring, A represents a covalent bond or a group of formula —CONHCH(Ar)— or —CH(Ar)NH—, and R$_1$, R$_2$, Y, n and p have the previously defined meaning.

4. A compound according to claim 1 of formula I wherein the 2-quinolylmethoxy radical is in the para or meta position of the benzene ring, A represents a covalent bond or a group of formula —CONHCH(Ar)— or —CH(Ar)NH—, R$_2$ represents hydrogen or methyl, and R$_1$, Y, n and p have the previously defined meaning.

5. 1-[3-[N-[p-(2-quinolylmethoxy)phenylacetyl]-]amino-3-phenylpropionyl]-4-[(2-methyl-3-pyridyl)-cyanomethyl]piperazine or a pharmaceutically-acceptable salt or solvate thereof.

6. 1-[3-[N-[p-(2-quinolylmethoxy)benzoyl]]amino-3-phenylpropionyl]-4-(3pyridylcyanomethyl)piperidine or a pharmaceutically-acceptable salt or solvate thereof.

7. 1-[N-[p-(2-quinolylmethoxy)phenylacetyl]-D-2-phenylglycinyl]-4-(3-pyridylcyanomethyl)piperidine or a salt or solvate thereof.

8. A pharmaceutical composition for administration to a mammal, which comprises a PAF and 5-lipoxygenase-inhibiting amount of a compound of Formula I:

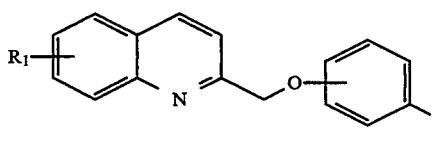 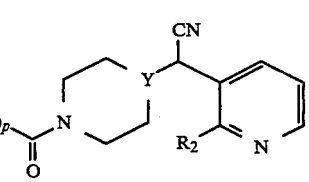

as a racemate, a diastereomer mixture or in optically active form wherein:

Y represents N or CH;
$R_1$ represents hydrogen, fluoro, chloro, difluoro or dichloro;
$R_2$ represents hydrogen or $C_{1-4}$ alkyl;
n is 0 or 1;
p is 0 or 1;
A represents a covalent bond or a group of formula —CONHCH(Ar)—, —NHCH(Ar)—, SO₂NHCH(Ar)—, —NHCONHCH(Ar)— or —OCONHCH(Ar)—, and when p is 1, A can also represent —CH(Ar)NH—;
Ar represents phenyl or phenyl substituted with halogen, $C_{1-4}$ alkyl, $C_{1-4}$ alkoxy or trifluoromethyl;
or a pharmaceutically acceptable salt or solvate thereof.

9. A composition according to claim 8 which comprises from about 5 to about 5000 mg of a compound of formula I, or a pharmaceutically acceptable salt or solvate thereof.

10. A composition according to claim 8 which comprises from about 25 to about 1000 mg of a compound of formula I, or a pharmaceutically acceptable salt or solvate thereof.

11. A pharmaceutical composition for topical application comprising a pharmaceutically-acceptable carrier and from about 0.5 to 10 percent by weight of a compound of formula I:

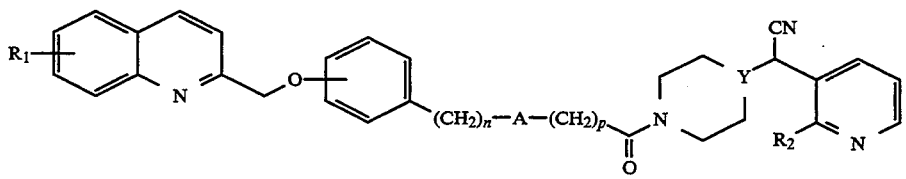

as a racemate, a diastereomer mixture or in optically active form wherein:

Y represents N or CH;
$R_1$ represents hydrogen, fluoro, chloro, difluoro or dichloro;
$R_2$ represents hydrogen or $C_{1-4}$ alkyl;
n is 0 or 1;
p is 0 or 1;
A represents a covalent bond or a group of formula —CONHCH(Ar)—, —NHCH(Ar)—, SO₂NHCH(Ar)—, —NHCONHCH(Ar)— or —OCONHCH(Ar)—, and when p is 1, A can also represent —CH(Ar)NH—;
Ar represents phenyl or phenyl substituted with halogen, $C_{1-4}$ alkyl, $C_{1-4}$ alkoxy or trifluoromethyl;
or a pharmaceutically acceptable salt or solvate thereof.

12. A method for treating a disease that involves an allergic or inflammatory response in a mammal in need thereof, the method comprising administering to said mammal an effective amount of a compound of formula I:

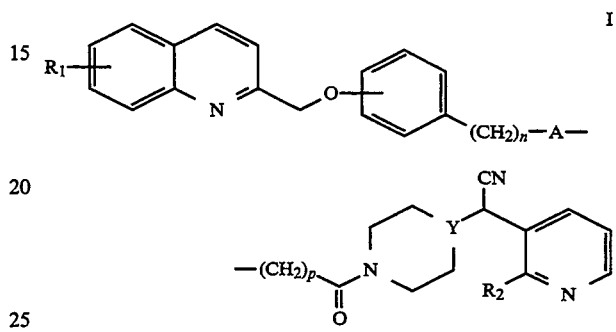

as a racemate, a diastereomer mixture or in optically active form wherein:

Y represents N or CH;
$R_1$ represents hydrogen, fluoro, chloro, difluoro or dichloro;
$R_2$ represents hydrogen or $C_{1-4}$ alkyl;
n is 0 or 1;
p is 0 or 1;
A represents a covalent bond or a group of formula —CONHCH(Ar)—, —NHCH(Ar)—, SO₂NHCH(Ar)—, —NHCONHCH(Ar)— or —OCONHCH(Ar)—, and when p is 1, A can also represent —CH(Ar)NH—;
Ar represents phenyl or phenyl substituted with halogen, $C_{1-4}$ alkyl, $C_{1-4}$ alkoxy or trifluoromethyl;
or a pharmaceutically acceptable salt or solvate thereof.

13. A method for treating septic shock, anaphylactic shock, hemorrhagic shock or myocardial ischemia in a mammal in need thereof, the method comprising administering to said mammal an effective amount of a compound of formula I:

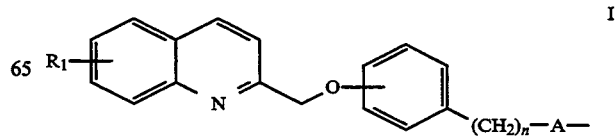

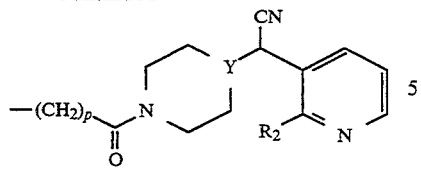

as a racemate, a diastereomer mixture or in optically active form wherein:

Y represents N or CH;

$R_1$ represents hydrogen, fluoro, chloro, difluoro or dichloro;

$R_2$ represents hydrogen or $C_{1-4}$ alkyl;

n is 0 or 1;

p is 0 or 1;

A represents a covalent bond or a group of formula —CONHCH(Ar)—, —NHCH(Ar)—, $SO_2$NHCH(Ar)—, —NHCONHCH(Ar)— or —OCONHCH(Ar)—, and when p is 1, A can also represent —CH(Ar)NH—;

Ar represents phenyl or phenyl substituted with halogen, $C_{1-4}$ alkyl, $C_{1-4}$ alkoxy or trifluoromethyl;

or a pharmaceutically acceptable salt or solvate thereof.

14. A method for treating inflammatory bowel disease in a mammal in need thereof, the method comprising administering to said mammal an effective amount of a compound of formula I:

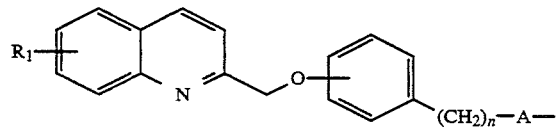

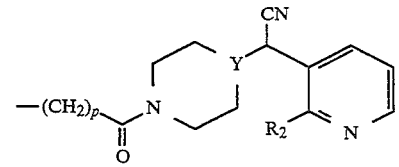

as a racemate, a diastereomer mixture or in optically active form wherein:

Y represents N or CH;

$R_1$ represents hydrogen, fluoro, chloro, difluoro or dichloro;

$R_2$ represents hydrogen or $C_{1-4}$ alkyl;

n is 0 or 1;

p is 0 or 1;

A represents a covalent bond or a group of formula —CONHCH (Ar)—, —NHCH(Ar)—, $SO_2$NHCH(Ar)—, —NHCONHCH(Ar)— or —OCONHCH(Ar)—, and when p is 1, A can also represent —CH(Ar)NH—;

Ar represents phenyl or phenyl substituted with halogen, $C_{1-4}$ alkyl, $C_{1-4}$ alkoxy or trifluoromethyl;

or a pharmaceutically acceptable salt or solvate thereof.

15. A method according to claim 12 wherein said disease is a member of the group consisting of asthma, dermatitis, urticaria, arthritis and psoriasis.

16. A method according to claim 12, 13 or 14 comprising administering to said mammal of from about 0.1 to about 50 mg/kg of body weight of a compound of formula I, or a pharmaceutically acceptable salt or solvate thereof.

17. A method according to claim 12, 13 or 14 comprising the administration of from about 0.5 to about 10 mg/kg of body weight of a compound of formula I, or a pharmaceutically acceptable salt or solvate thereof.

* * * * *